(12) United States Patent
Suzuki (10) Patent No.: US 10,274,613 B2
(45) Date of Patent: Apr. 30, 2019

(54) RADIATION IMAGING APPARATUS AND RADIATION IMAGING SYSTEM

(71) Applicant: CANON KABUSHIKI KAISHA, Tokyo (JP)

(72) Inventor: Masataka Suzuki, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 279 days.

(21) Appl. No.: 15/264,728

(22) Filed: Sep. 14, 2016

(65) Prior Publication Data

US 2017/0090044 A1    Mar. 30, 2017

(30) Foreign Application Priority Data

Sep. 29, 2015    (JP) .................................. 2015-192222

(51) Int. Cl.
*H01J 31/50*    (2006.01)
*G01T 1/20*    (2006.01)
(Continued)

(52) U.S. Cl.
CPC .......... *G01T 1/2018* (2013.01); *A61B 6/4283* (2013.01); *G01N 23/04* (2013.01); (Continued)

(58) Field of Classification Search
CPC ..... A61B 6/102; A61B 6/4283; A61B 6/4405; A61B 6/4233; A61B 6/4291; A61B 6/04; A61B 6/0492; A61B 6/4216; A61B 6/4452; A61B 6/4464; A61B 6/025; A61B 6/032; A61B 6/035; A61B 6/4085; A61B 6/44; A61B 6/4429; A61B 6/4441; A61B 6/4447; A61B 6/566; A61B 6/587; G01J 1/4228;
(Continued)

(56) References Cited

U.S. PATENT DOCUMENTS 8,834,022 B2    9/2014    Koyanagi
9,101,317 B2    8/2015    Kobayashi
(Continued)

FOREIGN PATENT DOCUMENTS

CN    102551763    7/2012
CN    102667620    9/2012
(Continued)

OTHER PUBLICATIONS

U.S. Appl. No. 15/225,976, filed Aug. 2, 2016.

*Primary Examiner* — Irakli Kiknadze
(74) *Attorney, Agent, or Firm* — Venable LLP (57) ABSTRACT

A radiation imaging apparatus is provided. The apparatus includes a radiation detection panel, a housing of a cuboid shape that accommodates the radiation detection panel. The housing has a front surface that the radiation enters, a rectangular back surface arranged on a side opposite to a side of the front surface, and four side surfaces configured to connect the front surface and the back surface. The apparatus further includes a grip portion which is concave toward the radiation detection panel, formed in a peripheral region on the back surface. The grip portion has at least one of a depth not less than one-half a distance between the front surface and the back surface, and a depth not less than a distance between the back surface and a center of gravity of the radiation imaging apparatus.

20 Claims, 7 Drawing Sheets

(51) Int. Cl.
*G03B 42/02* (2006.01)
*A61B 6/00* (2006.01)
*G01N 23/04* (2018.01)

(52) U.S. Cl.
CPC ............ *G03B 42/02* (2013.01); *A61B 6/4216* (2013.01); *A61B 6/4405* (2013.01); *A61B 6/566* (2013.01)

(58) Field of Classification Search
CPC ...... G01T 1/2018; G03B 42/04; G03B 42/02; G01N 23/04
See application file for complete search history.

(56) References Cited

U.S. PATENT DOCUMENTS

| | | | |
|---|---|---|---|
| 2002/0181659 A1 | 12/2002 | Watanabe et al. | ............ 378/189 |
| 2010/0044572 A1 | 2/2010 | Nishino | |
| 2010/0254517 A1 | 10/2010 | Watanabe | |
| 2011/0261928 A1* | 10/2011 | Ohta | ......... A61B 6/00 378/62 |
| 2012/0250826 A1 | 10/2012 | Watanabe et al. | |
| 2013/0077763 A1* | 3/2013 | Tagawa | ..... A61B 6/10 378/189 |
| 2014/0016757 A1* | 1/2014 | Tateishi | ..... G01T 1/16 378/189 |
| 2015/0293237 A1 | 10/2015 | Suzuki et al. | ........ G01T 1/2018 |
| 2015/0293239 A1* | 10/2015 | Miyoshi | .... G01T 7/00 250/394 |
| 2016/0084704 A1 | 3/2016 | Suzuki | ...... G01J 1/44 |
| 2017/0038252 A1* | 2/2017 | Suzuki | .......... A61B 6/102 |

FOREIGN PATENT DOCUMENTS

| | | |
|---|---|---|
| JP | 2002-082172 | 3/2002 |
| JP | 3577003 | 10/2004 |
| JP | 2010-133892 | 6/2010 |
| JP | 2015-051206 | 3/2015 |

* cited by examiner

RADIATION IMAGING APPARATUS AND RADIATION IMAGING SYSTEM

BACKGROUND OF THE INVENTION

Field of the Invention

The present invention relates to a radiation imaging apparatus and a radiation imaging system.

Description of the Related Art

A radiation imaging apparatus which obtains a radiation image of a target object by irradiating the target object with radiation and detecting an intensity distribution of the radiation transmitted through the target object is generally utilized in the field of an industrial non-destructive inspection or a medical diagnosis. In recent years, an imaging apparatus having a radiation detection panel which captures a digital radiation image is developed, making it possible to obtain an output image immediately.

In order to allow such an imaging apparatus to image a part quickly and widely, a thin and lightweight portable imaging apparatus, that is, an electronic cassette is developed. Particularly, in recent years, a wireless imaging apparatus free from cable connection is developed in order to improve portability.

Japanese Patent No. 3577003 describes an imaging apparatus whose grip portion having an opening is arranged outside an imaging region when viewed from a radiation incident direction in order to improve portability of the imaging apparatus. Japanese Patent Laid-Open No. 2015-51206 describes an imaging apparatus having, on its back surface, a concave portion which functions as a nonslip portion for a hand placed on the back surface.

If the grip portion having the opening is arranged outside the imaging region as in Japanese Patent No. 3577003, gripping performance is sufficient, and the portability is improved. It is impossible, however, to achieve a sufficient reduction in size of the imaging apparatus. On the other hand, if the nonslip portion made of the concave portion is formed on the back surface of the imaging apparatus as in Japanese Patent Laid-Open No. 2015-51206, a gap between the imaging region and an outer shape of the imaging apparatus can be reduced, facilitating downsizing. However, the gripping performance of the imaging apparatus may not be sufficient. As a result, it may be considered that the insufficient gripping performance causes an accidental drop or disables quick imaging.

SUMMARY OF THE INVENTION

The present invention provides, for example, a compact radiation imaging apparatus having good gripping performance.

According to one aspect of the present invention, a radiation imaging apparatus is provided. The apparatus includes a radiation detection panel configured to detect radiation, a housing of a cuboid shape configured to accommodate the radiation detection panel, wherein the housing has a front surface that the radiation enters, a rectangular back surface arranged on a side opposite to a side of the front surface with the radiation detection panel being sandwiched between the front surface and the back surface, and four side surfaces configured to connect the front surface and the back surface, and a grip portion which is concave toward the radiation detection panel, formed in a peripheral region on the back surface, wherein the grip portion has at least one of a depth not less than one-half a distance between the front surface and the back surface, and a depth not less than a distance between the back surface and a center of gravity of the radiation imaging apparatus.

Further features of the present invention will become apparent from the following description of exemplary embodiments (with reference to the attached drawings).

DESCRIPTION OF THE EMBODIMENTS

Various exemplary embodiments, features, and aspects of the invention will be described in detail below with reference to the drawings. Note that the same reference numerals denote the same members and elements throughout the drawings, and the repetitive description will be omitted.

First Embodiment

Figure 1A:
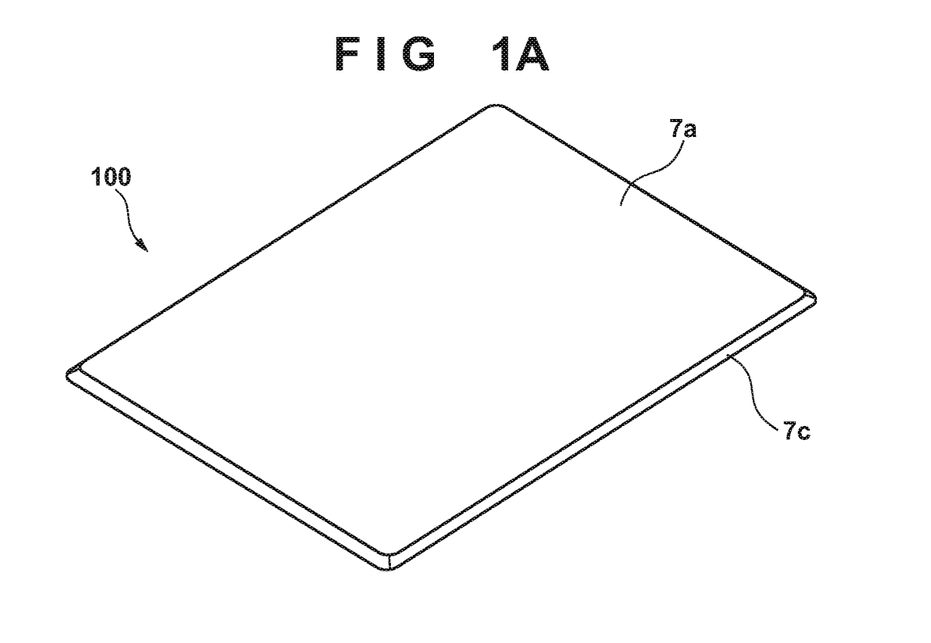
FIGS. 1A and 1B are views each showing an outer appearance of an imaging apparatus according to the first embodiment.
Figure 1B:
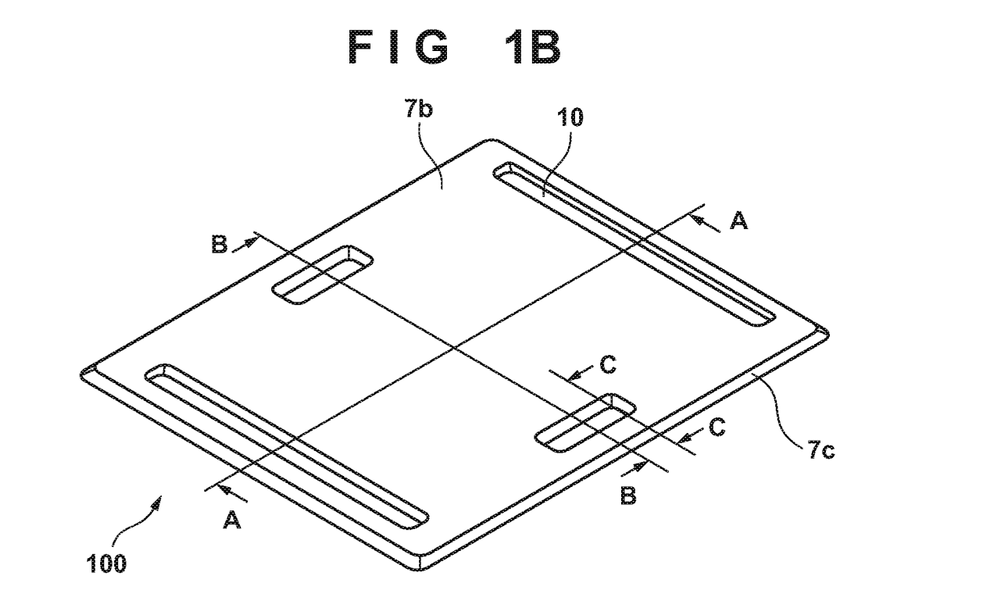
Figure 2A:
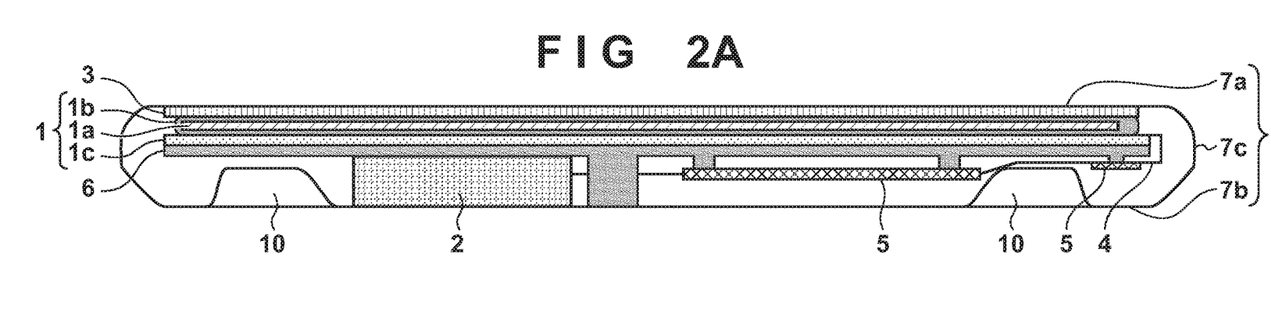
FIGS. 2A and 2B are sectional views each showing the internal arrangement of the imaging apparatus according to the first embodiment.
Figure 2B:
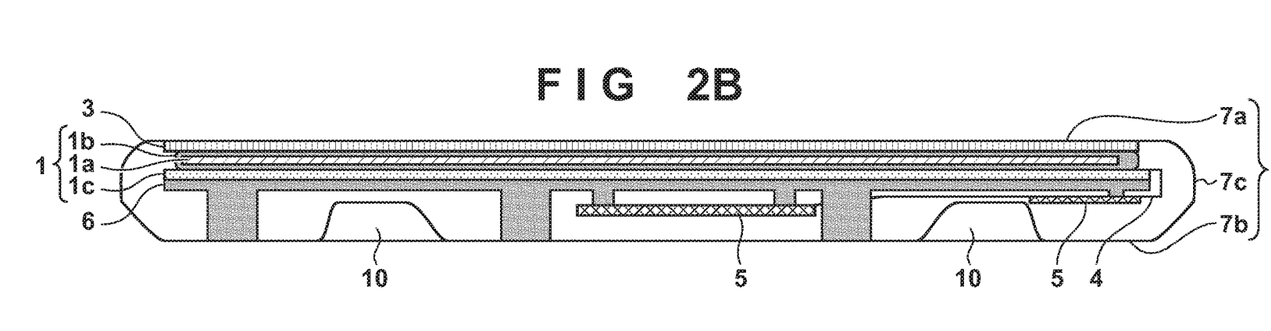

FIG. 1A shows the outer appearance of a radiation imaging apparatus (imaging apparatus) 100 including a radiation detection panel 1 when viewed from a front surface 7a and some of side surfaces 7c of a housing 7 having a cuboid shape that radiation enters. FIG. 1B is a perspective view showing a back surface 7b and some of the side surfaces 7c of the imaging apparatus 100 on the opposite side of FIG. 1A. As shown in FIG. 1B, concave grip portions 10 are formed on the back surface 7b of the housing 7 in the imaging apparatus 100 of the first embodiment. FIG. 2A is a sectional view showing the internal arrangement of the imaging apparatus 100 in an A-A direction of FIG. 1B. FIG. 2B is a sectional view showing the internal arrangement of the imaging apparatus 100 in a B-B direction of FIG. 1B. In general, the radiation of the imaging apparatus 100 is emitted by a radiation source 210 shown in FIG. 11, and the radiation detection panel 1 detects the radiation transmitted through an object. An image obtained by this imaging apparatus 100 is transferred to the outside, displayed on a monitor or the like, and used for a diagnosis or the like. FIG. 1B shows four grip portions 10 arranged in a peripheral region on the back surface 7b. Each pair of grip portions 10 extend in the first direction perpendicular to a corresponding pair of sides which define the outer shape of the back surface 7b and are parallel to each other. Each pair of grip portions 10 extend including a center position between the corresponding pair of sides.

The radiation detection panel 1 is of a so-called indirect conversion method and made of, for example, a sensor substrate 1c on which the large number of photoelectric conversion elements (sensors) are arranged, a phosphor layer (scintillator layer) 1a arranged on the sensor substrate 1c, and a phosphor protective film 1b. The phosphor protective film 1b is made of a material having low moisture permeability and protects the phosphor layer 1a. The radiation detection panel 1 is connected to a flexible circuit board 4. A control board 5 which reads out a detection signal from the radiation detection panel 1 and processes the readout detection signal is further connected to the flexible circuit board 4. As shown in FIG. 2A, the imaging apparatus 100 of the first embodiment includes a rechargeable battery 2 for supplying required power. The imaging apparatus 100 of the first embodiment also includes a connector 8 for feeding power from outside by wired connection or performing external communication. The control board 5 and the rechargeable battery 2 will collectively be called electric components. In the first embodiment, the rechargeable battery 2 is arranged between the back surface 7b and the radiation detection panel 1 in a center region surrounded by the peripheral region on the back surface 7b where the grip portions 10 are formed. The radiation detection panel 1 is not limited to but may be of a so-called direct conversion type formed by a conversion element portion where conversion elements made of a-Se or the like and electrical elements such as TFTs are arranged two-dimensionally.

The radiation detection panel 1 is supported by a support base 6 and included in the housing 7. The housing 7 has the rectangular front surface 7a that radiation enters, the rectangular back surface 7b on the opposite side of the front surface 7a with the radiation detection panel 1 being sandwiched between them, and four side surfaces 7c which connect the front surface 7a and the back surface 7b. A buffer material 3 is arranged between the front surface 7a and the radiation detection panel 1 to protect the radiation detection panel 1.

In order to improve gripping performance and portability, the imaging apparatus 100 of the first embodiment has the following arrangement. As shown in FIG. 1B, the housing 7 has, in the peripheral region along the respective sides of the rectangular back surface 7b, the gripping concave portions (grip portions) 10 concave toward the radiation detection panel 1. Having the grip portions 10 along the respective sides of the back surface 7b allows the imaging apparatus 100 to be gripped in various directions. This makes it easier to handle the imaging apparatus 100 and perform imaging quickly.

Figure 3:
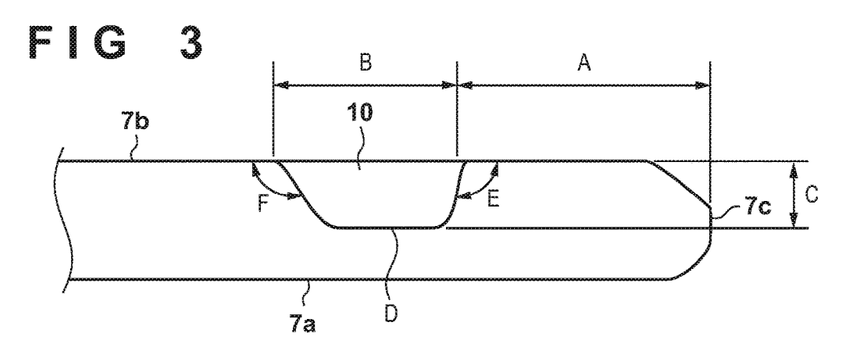
FIG. 3 is a sectional view showing the housing of the imaging apparatus according to the first embodiment.
Figure 4A:
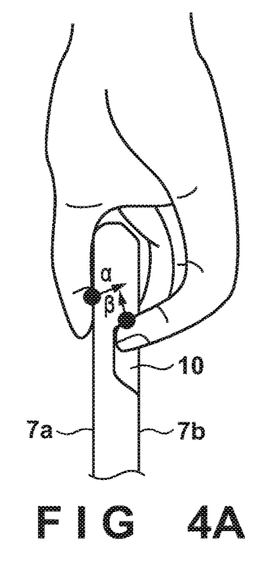
FIGS. 4A and 4B are views for explaining a state in which the imaging apparatus is gripped according to the first embodiment.

When viewed from a direction opposite to a radiation incident direction, a part or a maximum depth region (bottom surface) D of each of these grip portions 10 is within 60 mm from the side surface 7c of the housing 7. FIG. 3 is a sectional view showing the housing 7 of the imaging apparatus 100 in a C-C direction of FIG. 1B. FIG. 3 shows an example of the position and the shape of the grip portion 10. In the example of FIG. 3, a region (A region) from the side surface 7c of the housing 7 to the start edge of the grip portion 10 is 25 to 40 mm long, and a region (B region) between the start edge and end edge of the grip portion 10 is 15 to 30 mm long. The A region has a dimension of 25 to 40 mm because gripping forces α and β obtained when the panel-shaped imaging apparatus 100 is held on the ground almost vertically as shown in FIG. 4A are sufficiently applied to the imaging apparatus 100. It becomes difficult to grip the imaging apparatus 100 if the dimension of the A region is much larger or smaller than 25 to 40 mm. A problem that it is difficult to insert a finger arises if the B region is too small. On the contrary, a problem that an internal volume of the imaging apparatus 100 is decreased arises if the B region is too large. That is, when the A region and the B region have the above-described dimensions, it is possible to secure a volume for accommodating respective components of the imaging apparatus 100 while securing portability. More specifically, if the B region increases in an inward direction of the imaging apparatus 100, a space where the rechargeable battery 2 and the control board 5 shown in FIG. 2A are accommodated may be limited. Alternatively, a space where the support base 6 shown in FIG. 2B is arranged may be limited.

Figure 4B:
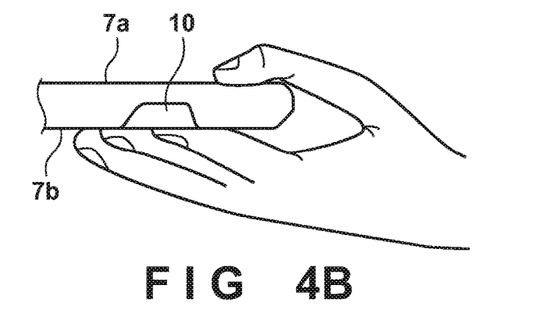

When the imaging apparatus 100 is held almost in parallel to the ground such as when the imaging apparatus 100 is inserted onto the back surface of an object or the like, it is also considered that the imaging apparatus 100 is held by stretching fingers as shown in FIG. 4B. In this case, if the sum of the dimensions of the A region and the B region is too large, it becomes difficult to support the imaging apparatus 100 stably, impairing operability. Therefore, the sum of the dimensions of the A region and the B region falls within 60 mm. This allows the imaging apparatus 100 to cope with various imaging operations quickly.

A depth C of the grip portion 10 is equal to or more than one-half the distance between the front surface 7a and the back surface 7b of the housing 7 such that the imaging apparatus 100 can easily rotate in a palmar direction when the imaging apparatus 100 is held almost vertically to the ground as shown in FIG. 4A. Alternatively, the depth C of the grip portion 10 is equal to or more than the distance between the back surface 7b of the housing 7 and the center of gravity of the imaging apparatus 100. By arranging the grip portion 10 to have this depth C, the moment at which the imaging apparatus 100 rotates in the palmar direction is produced easily, and the moment of rotation in a direction in which the imaging apparatus 100 escapes from the palm of a hand is reduced as much as possible. As a result, the imaging apparatus 100 is easily stabilized when gripped, making it possible to reduce a burden on a user. Even if it is impossible to make the depth C of the grip portion 10 deeper than the barycentric position of the imaging apparatus 100, the depth C of the grip portion 10 can be about 5 mm or more in order to increase the holding force β of the imaging apparatus 100 sufficiently.

In the first embodiment, the imaging apparatus 100 has a thickness of 13 to 16 mm so as to conform to the standard dimension of a general radiographic cassette in JISZ4905 (Photography-Medical radiographic cassettes/screens/films—Dimensions and specifications). Therefore, the depth C of the grip portion 10 is preferably more than 6.5 to 8.0 mm. The bottom surface (D region) of the grip portion 10 overlaps an imaging region where imaging is performed when viewed from the radiation incident direction. Therefore, the upper limit of the depth C of the grip portion 10 is defined to be about 10 to 14 mm so as to prevent the grip portion 10 from penetrating through the radiation detection panel 1. In order to make it easier to grasp the grip portion 10, the shapes of ends of the imaging apparatus 100 where the side surfaces 7c of the housing 7 cross the front surface 7a and the back surface 7b can be shapes to which R and a tilt are applied as shown in FIG. 3. Furthermore, as shown in FIG. 3, the grip portion 10 has the first side wall and the second side wall each extending in the first direction perpendicular to the pair of sides which define the outer shape of the back surface 7b and are perpendicular to each other, and a bottom surface which connects two side walls. The first direction is a longitudinal direction of each grip portion 10 shown in FIG. 1B and a direction perpendicular to a sheet surface in FIG. 3. Though depending on a frictional force, an angle (first angle) E formed by the back surface 7b and the side wall farther from the center of gravity of the imaging apparatus 100 suppresses a decrease in an internal space as much as possible and has magnitude from 120° (inclusive) to 90° (inclusive) in order to maintain a sufficient gripping force. An angle (second angle) F formed by the back surface 7b and the side wall facing the side wall that forms the angle E is larger than the angle E. Note that the angle F can be made larger than at least 90°. A tilt angle inside the grip portion 10 becomes moderate, making it easier to insert the hand. This makes it possible to obtain an effect of facilitating insertion of the hand into the grip portion 10 while suppressing the decrease in the internal space of the imaging apparatus 100 as much as possible when the imaging apparatus 100 is gripped as shown in FIG. 4A.

In order to prevent the imaging apparatus 100 from slipping out of the hand gripping the grip portion 10, a surface friction coefficient inside the concave portion of each grip portion 10 can be higher than a surface friction coefficient on the outer surface of the housing 7 without the grip portions 10. This can be implemented by changing the finish of the surface shape of the housing 7 or adhering a frictional sheet material or the like to each grip portion 10. The sheet material is made of, for example, a material such as rubber, a foaming resin, or the like. In order to increase the surface friction coefficient of each grip portion 10, the grip portion 10 may have unevenness on its surface. By increasing the friction coefficient of each grip portion 10 to be higher than that on the back surface 7b of the housing 7, the imaging apparatus 100 can be gripped stably by gripping it with the grip portions 10 while the imaging apparatus 100 is slipped smoothly and inserted easily when inserted onto the back surface or the like of a patient. As a result, handleability of the imaging apparatus 100 is improved.

Figure 5A:
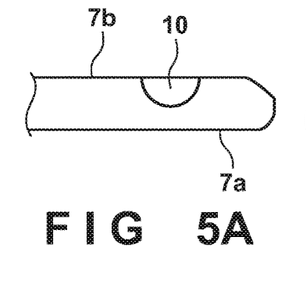
FIGS. 5A to 5C are sectional views each showing the grip portion of the imaging apparatus according to the first embodiment.
Figure 5B:
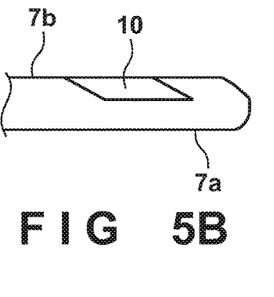
Figure 5C:
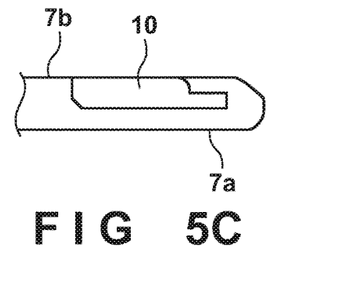

The grip portion 10 can also have various shapes as shown in FIGS. 5A to 5C, in addition to the shape shown in FIG. 3. In FIG. 5A, the sectional shape of the grip portion 10 is a semicircle in order to increase an internal volume of the housing 7 of the imaging apparatus 100 as much as possible. In FIG. 5B, the sectional shape of the grip portion 10 is a parallelogram. In FIG. 5C, the sectional shape of the grip portion 10 is a polygon. When the grip portion 10 has the sectional shape as in FIG. 5B or 5C, the direction of the holding force β changes when the imaging apparatus 100 is held almost vertically to the ground as shown in FIG. 4A, making it easier to hold the imaging apparatus 100 in a rotation direction toward the palm of the hand and enabling stable gripping. In the first embodiment, the electric components such as the rechargeable battery 2 and the control board 5 are not arranged between the grip portions 10 and the radiation detection panel 1.

In the grip portions 10, by coupling a back-surface member having the back surface 7b of the housing 7 and the support base 6 which supports the radiation detection panel 1 to each other with screws, an adhesive, or the like, it is possible to integrate the housing 7 and the support base 6 with each other, improving rigidity of the imaging apparatus 100. When the electric components and the like are arranged between the grip portions 10 and the radiation detection panel 1, for example, a spacer or a foaming material serving as a buffer material can be arranged between the electric components and the grip portions 10 in order to avoid damage to the electric components or the like even if a large load is imposed on them. An arrangement may also be possible in which heat radiation to the outside is performed efficiently by arranging a heat radiating material between the electric components and the grip portions 10.

Figure 6:
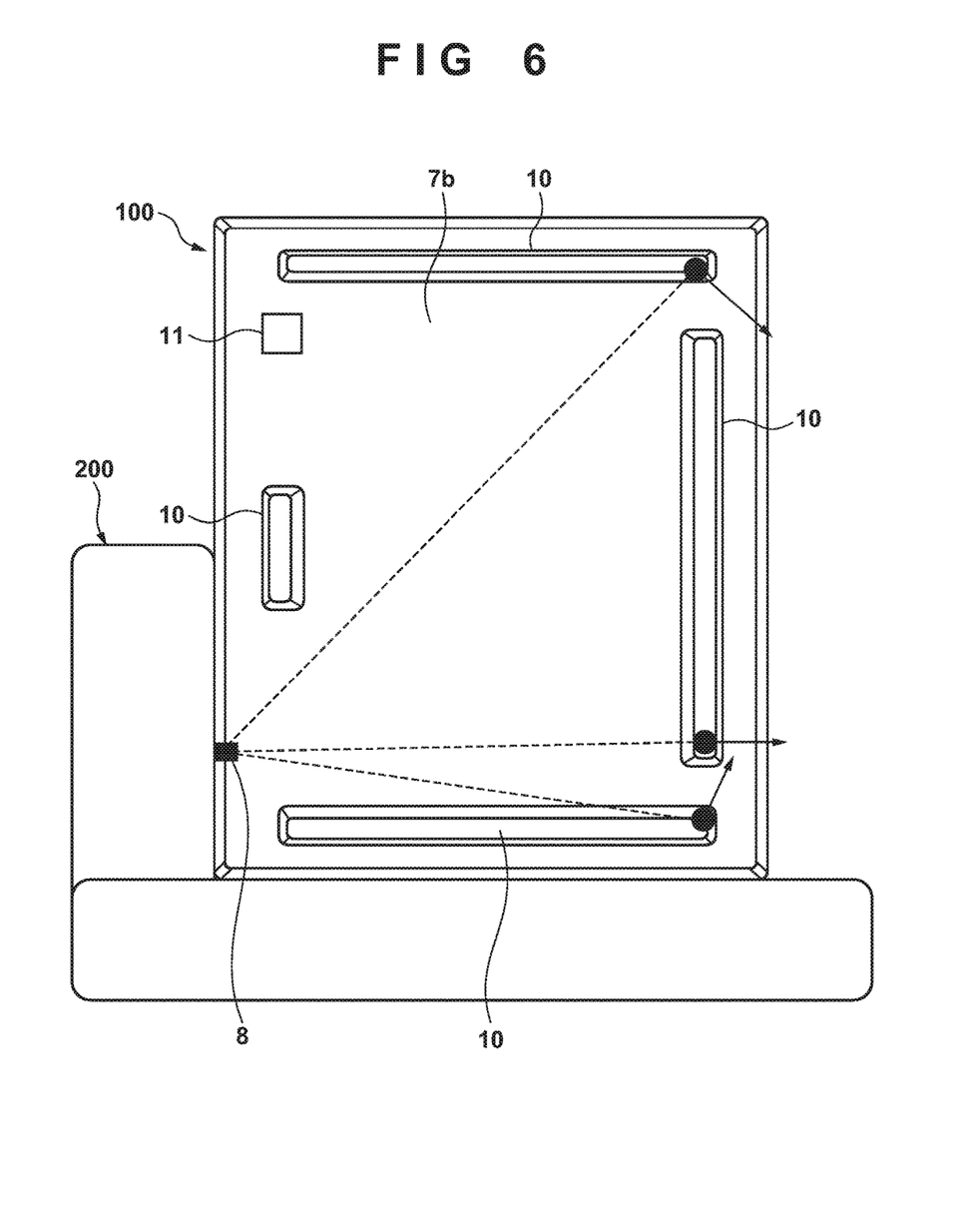
FIG. 6 is a view for explaining a state when the imaging apparatus is removed from a cradle according to the first embodiment.

When the imaging apparatus 100 is viewed from the direction opposite to the radiation incident direction, the external communication connector 8 can be arranged on the side surface 7c as shown in FIG. 6. In this case, the peripheral region where four grip portions 10 are arranged is divided into the first peripheral region with the side surface 7c on which the connector 8 is arranged as a boundary line and the second peripheral region without the side surface 7c on which the connector 8 is arranged as the boundary line. As shown in FIG. 6, each grip portion 10 formed in the first peripheral region with the side surface 7c on which the connector 8 is arranged as the boundary line is longer than the grip portion 10 formed in the second peripheral region, and they are different in shape. That is, each grip portion 10 formed in the first peripheral region with the side surface 7c on which the connector 8 is arranged as the boundary line may extend near corners of the back surface 7b. It is considered to utilize, for example, a charging cradle 200 external to the imaging apparatus 100 to charge the imaging apparatus 100 because it is possible to facilitate handling at this time. The connector 8 can have a holding force by using a magnet or the like. It is possible, however, to facilitate removal by applying a force of rotating or pulling the imaging apparatus 100 from the cradle 200 by using the long grip portions 10 as shown in FIG. 6. It is also possible to obtain an advantage of facilitating quick imaging because a grippable region increases by making the grip portions 10 longer, and it becomes easier to handle the imaging apparatus 100.

Figure 7:
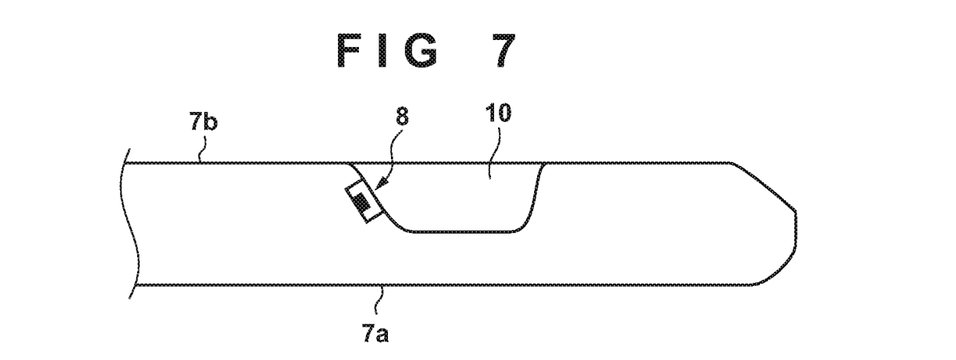
FIG. 7 is a sectional view showing the grip portion of the imaging apparatus according to the first embodiment.

In FIG. 6, the external communication connector 8 is provided on the side surface 7c of the housing 7. As shown in FIG. 7, however, the external communication connector 8 may be provided inside the grip portion 10. This arranges the connector 8 at a position which can hardly receive an external force directly, making it easier to protect the connector 8. Like FIG. 3, FIG. 7 is a sectional view in the C-C direction of FIG. 1B. As shown in FIG. 7, the connector 8 is preferably arranged on a side wall opposite to a side wall of the grip portion 10 touched when gripping the imaging apparatus 100.

When gripping the imaging apparatus 100 by using the grip portion 10, it is assumed, as shown in FIGS. 4A and 4B, that the hand gripping the imaging apparatus 100 covers the grip portion 10 and the periphery of the side of the imaging apparatus 100 close to that grip portion 10. For this reason, a switch 11 or the like is provided so as not to be arranged in a region of the imaging apparatus 100 which is covered with the hand gripping the imaging apparatus 100. This is because an erroneous operation is assumed to be induced by arranging the switch 11 or the like in the region which is covered with the hand gripping the imaging apparatus 100. In the first embodiment, the switch 11 is also arranged in a region which has no grip portion 10 in its neighborhood and is not covered with the hand gripping the imaging apparatus 100 as shown in FIG. 6.

It may become difficult, by covering an LED and a loudspeaker each indicating a status display with the hand, to determine their statuses. The radiation performance of an antenna is influenced by being covered with the hand. Therefore, the antenna may be arranged leaving a space of a half wavelength or more from the region covered with the hand. Also, the loudspeaker prevents diffusion of a sound because of an influence by the hand gripping the imaging apparatus 100. If the wired connection connector 8 is arranged at a position covered with the hand, a state is set in which it is difficult to grip the imaging apparatus 100 when a cable is connected to the connector 8. Therefore, like the switch 11, the LED and the loudspeaker each indicating the status display, the antenna which performs infrared communication or wireless communication, and the connector 8 which performs wired connection are also arranged in the region which is not covered with the hand gripping the imaging apparatus 100.

The imaging apparatus 100 of the first embodiment having the above-described arrangement implements both an improvement in the gripping performance and downsizing by providing the grip portions 10 in the imaging region.

Second Embodiment

Figure 8:
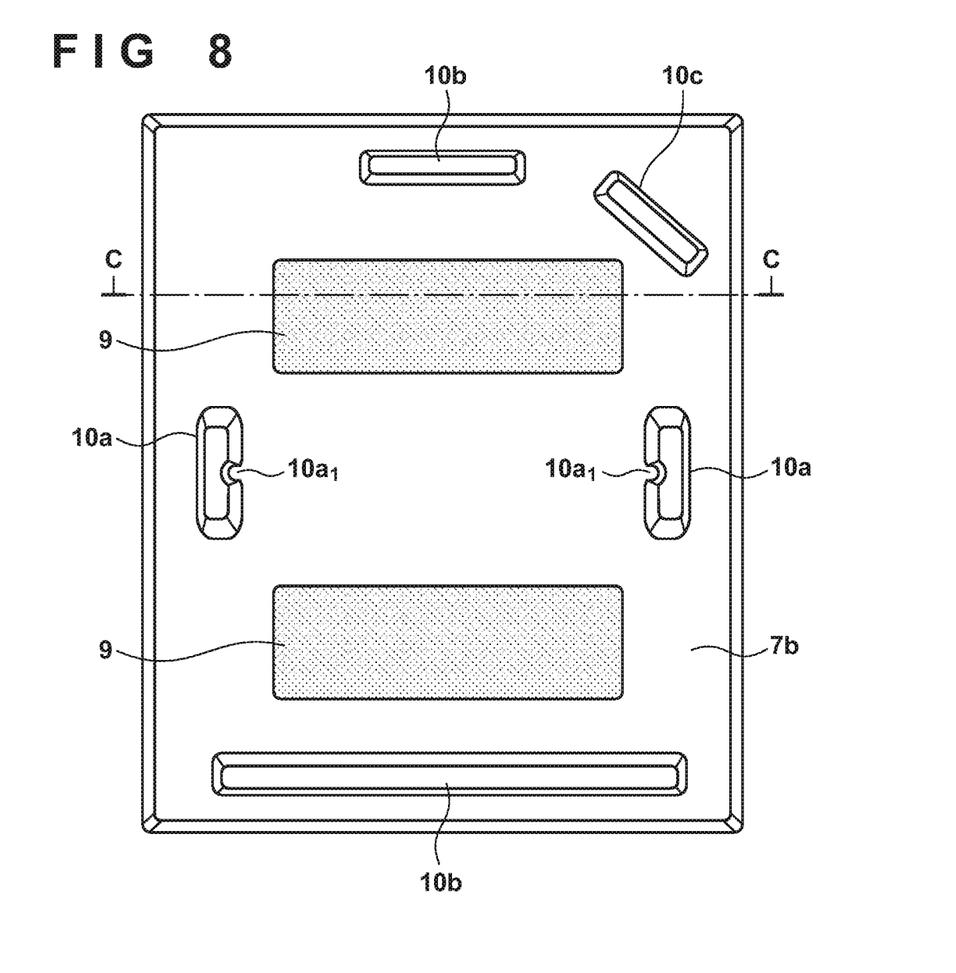
FIG. 8 is a view showing the outer appearance of an imaging apparatus when viewed from a back surface according to the second embodiment.

In the first embodiment, the compact imaging apparatus having the good gripping performance according to one embodiment has been described. In the second embodiment, in order to improve portability of an imaging apparatus, an attempt is made to reduce the weight of the apparatus, in addition to making it easier to grip. FIG. 8 is a view showing an imaging apparatus 100 when viewed from an opposite side to a radiation incident direction according to the second embodiment. At least some of grip portions 10 of the second embodiment have, for example, the same shape as the grip portions 10 of the first embodiment. No moment is produced when the imaging apparatus 100 is gripped by inserting fingers into the centers of a spacing between a pair of sides of a back surface 7b including the grip portions 10 on either side, making it possible to grip the imaging apparatus 100 stably. In the second embodiment, the centers of the grip portions 10 can be detected by tactile perception even if the imaging apparatus 100 is hidden, for example, behind an object, and the grip portions 10 are invisible. In the second embodiment, parts 10a1 indicating the centers are formed in some grip portions 10a. For example, as shown in FIG. 8, each part 10a1 indicating the center is a projection or a dent. Each part 10a1 indicating the center may have smoothness different from that of the remaining part of each grip portion 10a. Further, each part 10a1 indicating the center may be formed by partially changing the depth or the shape of a sectional shape of the grip portion 10a.

In FIG. 8, like the grip portions 10 of the first embodiment, a longitudinal direction of each of four grip portions 10 out of five grip portions 10 is parallel to a side which defines the outer shape of the back surface 7b. Out of four grip portions 10, two are grip portions 10b without the parts 10a1 each indicating the center like the grip portions 10 of the first embodiment, and the remaining two are the grip portions 10a having the parts 10a1 each indicating the center. A grip portion 10c as the remaining one grip portion has the same structure and shape as each grip portion 10 of the first embodiment, but is arranged at the corner of the back surface 7b and formed such that its longitudinal direction crosses each side which defines the outer shape of the back surface 7b. This one grip portion 10c is formed such that a direction (widthwise direction) perpendicular to the longitudinal direction of a concave portion is oriented to the center of gravity or the center of the imaging apparatus 100.

Figure 9:
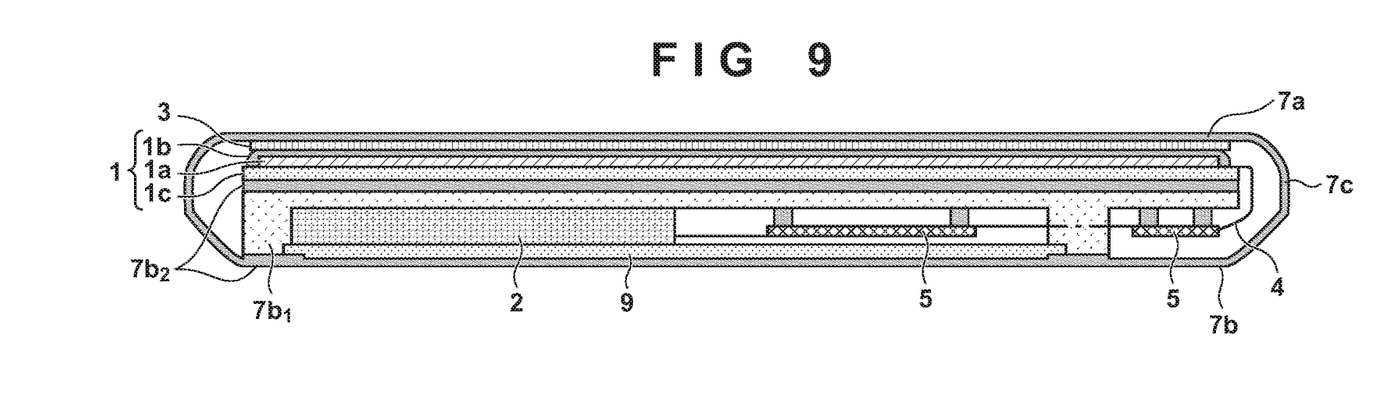
FIG. 9 is a sectional view showing the internal arrangement of the imaging apparatus according to the second embodiment.

FIG. 9 is a sectional view showing the imaging apparatus 100 shown in FIG. 8 in a C-C direction. As in the first embodiment, a control board 5 which performs a process of controlling readout of a radiation detection panel 1 or outputting electricity is connected to the radiation detection panel 1 via a flexible circuit board 4, and a housing 7 which accommodates them is provided. Similarly, a rechargeable battery 2 for supplying power is also provided.

The inner surface of a back-surface member, on the side of the radiation detection panel 1, having the back surface 7b of the housing 7 of the second embodiment has a support surface which supports the radiation detection panel 1. Concave portions where electric components are to be arranged are formed on the outer surface of the back-surface member on an opposite side to the radiation detection panel 1. This allows the support base 6 of the first embodiment and a part of the back-surface member to be integrated with each other, facilitating a weight reduction. Further, the large number of concave portions are formed, in the housing 7, by concave portions serving as the grip portions 10 and the concave portions where the electric components and the like are to be arranged, making it possible to increase bending rigidity (flexural rigidity) of the housing 7. Furthermore, the back-surface member has an arrangement having a multi-layered structure of a core layer 7b1 and skin layers 7b2 sandwiching the core layer as shown in FIG. 9, obtaining an arrangement that further facilitates the weight reduction. Each skin layer 7b2 can be formed by a fiber-reinforced resin such as CFRP, a fiber-reinforced metal, or a metal alloy such as an aluminum alloy or a magnesium alloy. The core layer 7b1 can be formed by a foaming resin, or a structure having a honeycomb structure or a lattice structure. In this embodiment, a detachable access cover (cover member) 9 is further provided in the concave portions where the electric components and the like are to be arranged so as not to expose the electric components to the outside.

Figure 10:
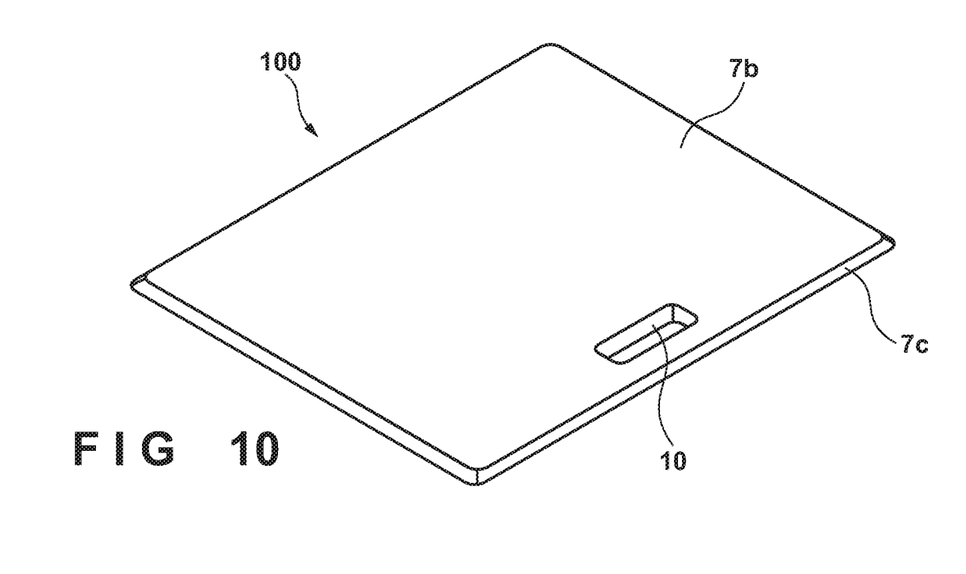
FIG. 10 is a view showing the outer appearance of the imaging apparatus according to the second embodiment.

The imaging apparatus 100 of the second embodiment having the above-described arrangement implements both an improvement in gripping performance and downsizing as in the first embodiment, and further improves the weight reduction than in the first embodiment. The imaging apparatus 100 including the plurality of grip portions 10 has been described in each of the first and second embodiments. However, the present invention is not limited to this. As shown in FIG. 10, the number of grip portions 10 formed in the imaging apparatus 100 may be one.

[Radiation Imaging System]

Figure 11:
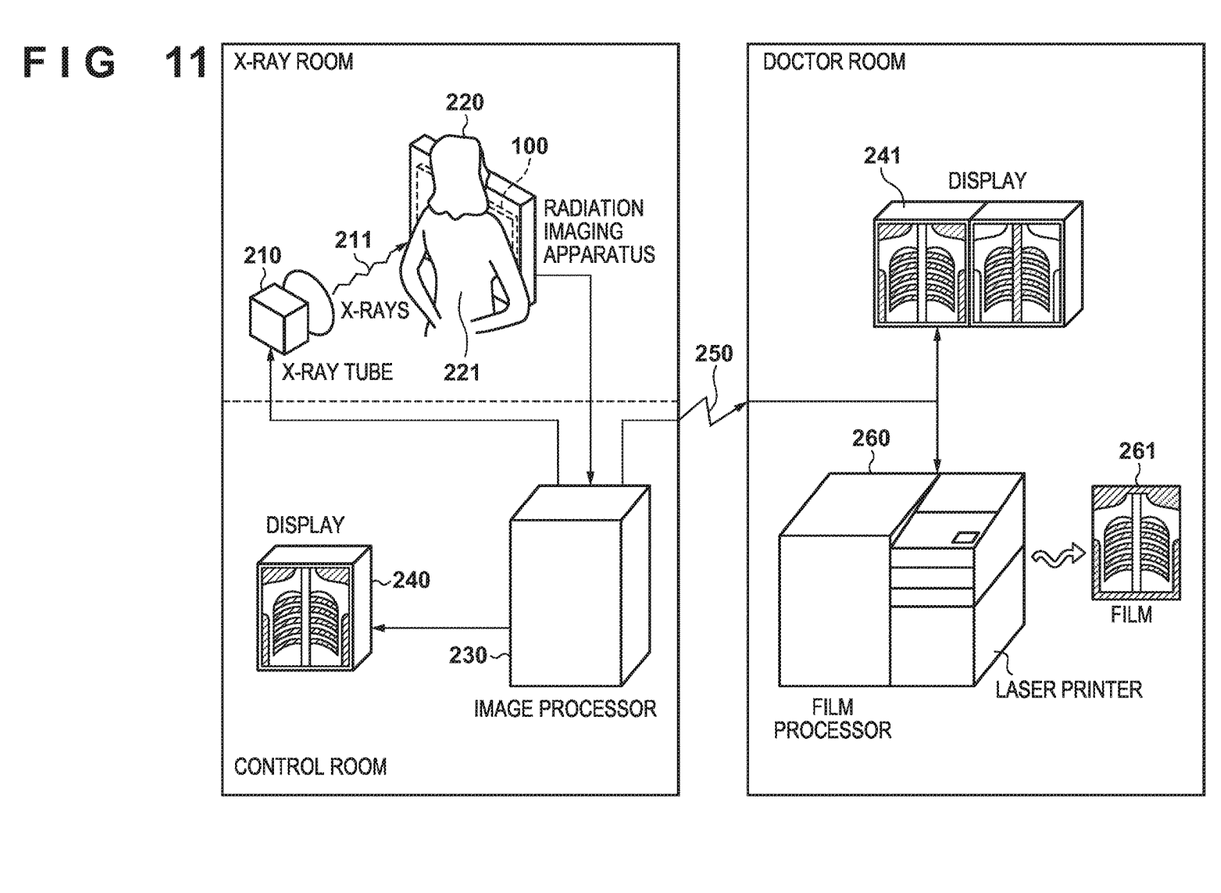
FIG. 11 shows views of a radiation imaging system according to an embodiment of the present invention.

FIG. 11 is directed to a radiation imaging system including the above-described radiation imaging apparatus 100. As shown in FIG. 11, X-rays (radiation) 211 generated in an X-ray tube (radiation source) 210 are transmitted through a chest 221 of a patient or an object 220, and enter a radiation imaging apparatus 100. These incident X-rays contain information of the interior of the body of the patient 220. The scintillator (phosphor) emits light as the X-rays enter, and a sensor (photoelectric conversion element) of a sensor panel photoelectrically converts this emitted light, obtaining electrical information. This electrical information is converted into a digital signal. A signal processing unit (image processor) 230 performs image processing of the signal. It is possible to observe the resultant image on a display unit (display) 240.

The information that has undergone image processing by the image processor 230 can be transferred to a remote place through a transmission processing unit 250 such as a network like a telephone, a LAN, or the Internet. Therefore, the information which has undergone image processing by the image processor 230 can be displayed on a display unit (display) 241 in another place such as a doctor room or saved in a recording unit such as an optical disk, allowing a doctor in a remote place to make diagnosis. The information which has undergone image processing by the image processor 230 can also be recorded in a film 261 by a film processor 260.

A radiation detection apparatus of the present invention can be applied to a medical radiation detection apparatus or an apparatus, other than a medical apparatus, used for an analysis or an inspection which utilizes radiation such as a nondestructive inspection apparatus.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-192222, filed Sep. 29, 2015, which is hereby incorporated by reference herein in its entirety.

What is claimed is:

1. A radiation imaging apparatus comprising:
   a radiation detection panel configured to detect radiation; and
   a housing of a cuboid shape configured to accommodate the radiation detection panel, the housing having a front surface that the radiation enters, a rectangular back surface arranged on a side opposite to a side of the front surface with the radiation detection panel being sandwiched between the front surface and the back surface, and four side surfaces configured to connect the front surface and the back surface, the housing further providing a grip portion which is concave toward the radiation detection panel, formed in a peripheral region on the back surface, wherein
   the grip portion has at least one of a depth not less than one-half a distance between the front surface and the back surface, and a depth not less than a distance between the back surface and a center of gravity of the radiation imaging apparatus.

2. The apparatus according to claim 1, further comprising an electric component arranged between the back surface and the radiation detection panel in a center region surrounded by the peripheral region.

3. The apparatus according to claim 1, further comprising a connector arranged on at least one of the side surfaces and configured to perform one of power feeding from outside and external communication,
   wherein the peripheral region includes a first peripheral region with the at least one side surface as a boundary line and a second peripheral region without the at least one side surface as the boundary line, and
   the grip portion includes a first grip portion arranged in the first peripheral region and a second grip portion arranged in the second peripheral region, the first grip portion and the second grip portion having different shapes.

4. The apparatus according to claim 1, wherein the grip portion includes a first side wall and a second side wall each extending in a first direction perpendicular to a pair of sides which define an outer shape of the back surface and are parallel to each other and a bottom surface which connects the first side wall and the second side wall, and extends including a center position between the pair of sides.

5. The apparatus according to claim 4, wherein a first angle formed by the back surface and the side wall, out of the first side wall and the second side wall, farther from the center of gravity of the radiation imaging apparatus is not more than 120°.

6. The apparatus according to claim 5, wherein a second angle formed by the back surface and the side wall, out of the first side wall and the second side wall, closer to the center of gravity of the radiation imaging apparatus is larger than the first angle.

7. The apparatus according to claim 4, wherein a part indicating the center position between the pair of sides is formed on at least one of the first side wall, the second side wall, and the bottom surface.

8. The apparatus according to claim 7, wherein the part is one of a projection and a dent.

9. The apparatus according to claim 7, wherein the part has smoothness different from that of a remaining part of the grip portion.

10. The apparatus according to claim 1, wherein the grip portion is arranged at a corner of the back surface, and includes a first side wall and a second side wall each extending in a direction crossing each of four sides which define an outer surface of the back surface, and a bottom surface which connects the first side wall and the second side wall.

11. The apparatus according to claim 10, wherein a first angle formed by the back surface and the side wall, out of the first side wall and the second side wall, farther from the center of gravity of the radiation imaging apparatus is not more than 120°.

12. The apparatus according to claim 11, wherein a second angle formed by the back surface and the side wall, out of the first side wall and the second side wall, closer to the center of gravity of the radiation imaging apparatus is larger than the first angle.

13. The apparatus according to claim 1, further comprising a connector arranged inside the grip portion and configured to perform one of power feeding from outside and external communication.

14. The apparatus according to claim 1, further comprising a support base configured to support the radiation detection panel,
   wherein in the grip portion, the support base is coupled to a back-surface member having the back surface in the housing.

15. The apparatus according to claim 1, further comprising a support base configured to support the radiation detection panel; and
   an electric component arranged between the support base and the grip portion, wherein
   at least one of a buffer material, a spacer, and a heat radiating material is arranged between the grip portion and the electric component.

16. The apparatus according to claim 1, wherein in a center region surrounded by the peripheral region on the back surface, a concave portion concave toward the radiation detection panel is formed, and an electric component is arranged in the concave portion.

17. The apparatus according to claim 16, further comprising a cover member configured to cover the concave portion.

18. The apparatus according to claim 1, wherein a back-surface member having the back surface in the housing has a multi-layered structure of a core layer and skin layers sandwiching the core layer.

19. A radiation imaging system, comprising:
a radiation imaging apparatus;
a signal processing unit configured to process a signal from the radiation imaging apparatus;
a display unit configured to display the signal from the signal processing unit; and
a radiation source configured to generate radiation, wherein
the radiation imaging apparatus comprises a radiation detection panel configured to detect radiation and a housing of a cuboid shape configured to accommodate the radiation detection panel,
the housing having a front surface that the radiation enters, a rectangular back surface arranged on a side opposite to a side of the front surface with the radiation detection panel being sandwiched between the front surface and the back surface, and four side surfaces configured to connect the front surface and the back surface, the housing further providing a grip portion which is concave toward the radiation detection panel, formed in a peripheral region on the back surface,
the grip portion having at least one of a depth not less than one-half a distance between the front surface and the back surface, and a depth not less than a distance between the back surface and a center of gravity of the radiation imaging apparatus.

20. A radiation imaging apparatus comprising:
a radiation detection panel configured to detect radiation;
a housing of a cuboid shape configured to accommodate the radiation detection panel, the housing having a front surface that the radiation enters, a rectangular back surface arranged on a side opposite to a side of the front surface with the radiation detection panel being sandwiched between the front surface and the back surface, and four side surfaces configured to connect the front surface and the back surface;
an electric component arranged between the back surface and the radiation detection panel; and
a grip portion which is concave toward the radiation detection panel, formed in a peripheral region on the back surface, wherein
the grip portion has at least one of a depth not less than one-half a distance between the front surface and the back surface, and a depth not less than a distance between the back surface and a center of gravity of the radiation imaging apparatus, and
none of the electric component is arranged between the grip portion and the radiation detection panel.

* * * * *